United States Patent
Okihara (10) Patent No.: US 12,318,596 B2
(45) Date of Patent: Jun. 3, 2025

(54) SYRINGE CAP, SYRINGE ASSEMBLY, AND PRE-FILLED SYRINGE

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 923 days.

(21) Appl. No.: 17/448,763

(22) Filed: Sep. 24, 2021

(65) Prior Publication Data

US 2022/0008659 A1 Jan. 13, 2022

Related U.S. Application Data

(63) Continuation of application No. PCT/JP2019/012948, filed on Mar. 26, 2019.

(51) Int. Cl.
*A61M 5/32* (2006.01)
*A61M 5/34* (2006.01)
*A61M 5/31* (2006.01)

(52) U.S. Cl.
CPC ......... *A61M 5/3202* (2013.01); *A61M 5/347* (2013.01); *A61M 2005/3109* (2013.01); *A61M 2005/3125* (2013.01)

(58) Field of Classification Search
CPC ............ A61M 5/3202; A61M 5/347; A61M 2005/3109; A61M 2005/3125; A61M 5/178; A61M 5/5086; A61M 39/20; A61M 2005/3103; A61M 2005/3104; A61M 2005/3106; A61M 5/3134; A61M 2005/3117; A61M 2005/3118; A61M 2005/312
See application file for complete search history.

(56) References Cited

U.S. PATENT DOCUMENTS

2010/0305511 A1 12/2010 Thibault et al.
2013/0030380 A1 1/2013 Abe et al.
(Continued)

FOREIGN PATENT DOCUMENTS

CN 101801443 A 8/2010
CN 102821804 A 12/2012
(Continued)

OTHER PUBLICATIONS

Office Action (The First Office Action) issued Jan. 28, 2023, by the National Intellectual Property Administration, P.R. China in corresponding Chinese Patent Application No. 201980092399.1 and an English translation of the Office Action. (16 pages).
(Continued)

*Primary Examiner* — Nathan R Price
*Assistant Examiner* — Fatimata Sahra Diop
(74) *Attorney, Agent, or Firm* — Buchanan Ingersoll & Rooney PC (57) ABSTRACT

A syringe assembly of a pre-filled syringe that includes a syringe cap having a tubular cover member that covers a cap body. The cover member includes a substantially opaque first tubular section and a second tubular section having a display section. An inner peripheral surface of the cover member is roughened at least from a vicinity of a distal end of the first tubular section to a vicinity of a proximal end section of a proximal end tubular section.

18 Claims, 4 Drawing Sheets

(56) References Cited

U.S. PATENT DOCUMENTS

| | | |
|---|---|---|
| 2015/0174338 A1 | 6/2015 | Takemoto |
| 2016/0151544 A1 | 6/2016 | Nakano et al. |
| 2016/0151584 A1 | 6/2016 | Deleuil et al. |
| 2019/0046736 A1 | 2/2019 | Okihara |
| 2019/0099557 A1* | 4/2019 | Potdar ................. A61M 5/3134 |
| 2019/0217020 A1 | 7/2019 | Okihara |

FOREIGN PATENT DOCUMENTS

| | | | |
|---|---|---|---|
| CN | 104602740 A | 5/2015 | |
| CN | 105848698 A | 8/2016 | |
| CN | 108883233 A | 11/2018 | |
| EP | 2 878 321 A1 | 6/2015 | |
| JP | 2013078442 A * | 5/2012 | |
| JP | 5075982 B2 | 11/2012 | |
| JP | 2016101240 A | 6/2016 | |
| JP | 2016524981 A | 8/2016 | |
| WO | 2015/007900 A1 | 1/2015 | |
| WO | WO-2017179313 A1 * | 10/2017 | ............ A61M 39/20 |
| WO | 2018061948 A1 | 4/2018 | |

OTHER PUBLICATIONS

International Search Report (PCT/ISA/210) with English translation mailed on Jun. 25, 2019, by the Japanese Patent Office as the International Searching Authority for International Application No. PCT/JP2019/012948.
The extended European Search Report issued Jan. 28, 2022, by the European Patent Office in corresponding European Patent Application No. 19921884.3-1122. (9 pages).

* cited by examiner

SYRINGE CAP, SYRINGE ASSEMBLY, AND PRE-FILLED SYRINGE

CROSS-REFERENCES TO RELATED APPLICATIONS

This application is a continuation of International Application No. PCT/JP2019/012948 filed on Mar. 26, 2019, the entire content of which is incorporated herein by reference.

FIELD OF THE DISCLOSURE

The present disclosure generally relates to a syringe cap, a syringe assembly, and a pre-filled syringe, in which the syringe cap is detachable from a syringe body that includes: a body section capable of internally accommodating a drug; and a nozzle section protruding in a distal end direction from a distal end section of the body section and having a drug discharge port at a distal end.

BACKGROUND DISCUSSION

WO 2018/061948 A discloses a syringe cap including a cap body and a tubular cover member covering the cap body. The cap body has a mounting section that is mountable to a nozzle section of a syringe body, and a viewing section located on a distal end side from the mounting section. The cover member includes a substantially opaque first tubular section and a substantially transparent second tubular section extending in the distal end direction from an opening at a distal end of the first tubular section.

The cap body is at a first position where the viewing section is located in the first tube section in an unopened state of the syringe cap. At this time, the viewing section is substantially invisible. Whereas, when the mounting section of the syringe cap removed from the syringe body is brought close to the nozzle section, the cap body is displaced from the first position to a second position where the viewing section protrudes in the distal end direction from the distal end of the first tubular section, by being pushed in the distal end direction by the nozzle section. That is, the viewing section becomes substantially visible, which makes it possible to discriminate between an unopened state and an opened state of the syringe cap.

However, in the syringe cap as described in WO 2018/061948 A, in a case where an outer peripheral surface of the cap body and an inner peripheral surface of the cover member come into contact with each other, a frictional resistance may prevent smooth movement of the cap body from the first position to the second position.

SUMMARY

A syringe cap, a syringe assembly, and a pre-filled syringe in which a cap body can be rather smoothly displaced from a first position to a second position, and an unopened state and an opened state of the syringe cap can be rather easily and reliably discriminated.

In accordance with one aspect of the present disclosure a syringe cap that can be detachable from a syringe body, the syringe body including: a body section capable of internally accommodating a drug; and a nozzle section protruding in a distal end direction from a distal end section of the body section and having a drug discharge port at a distal end. The syringe cap includes a cap body made by an elastic material; and a cover member having a tubular shape and covering the cap body. The cap body includes: a mounting tube section having a tubular shape, having a sealing section that liquid-tightly seals the drug discharge port at a distal end, and being capable of accommodating the nozzle section; an abutting section located at a proximal end section of the mounting tube section and being capable of abutting with a distal end section of the nozzle section; and a viewing section arranged at a distal end of the mounting tube section. The cover member includes: a first tubular section being substantially opaque, and having an opening at a distal end and a first space capable of internally housing the viewing section; a second tubular section arranged at a distal end of the first tubular section; a proximal end tubular section extending in a proximal end direction from a proximal end of the first tubular section and having a housing space capable of internally housing the mounting tube section; and an engagement protrusion protruding from an inner peripheral surface of a proximal end section of the proximal end tubular section and configured to engage with the proximal end section of the cap body to prevent detachment of the cap body in a proximal end direction from the cover member. The second tubular section has: an annular peripheral wall section extending in a distal end direction from the distal end of the first tubular section; a distal end wall arranged at a distal end of the annular peripheral wall section; and a second space defined by the annular peripheral wall section, the distal end wall, and an inner edge of the distal end of the first tubular section. The annular peripheral wall section has a display section for visual inspection of an inside of the second space from an outside. The cap body can displace, along a center axis of the cover member in the cover member, from a first position where the viewing section is located in the first space of the first tubular section to a second position where the viewing section is arranged in the second space. The sealing section is capable of liquid-tightly sealing the nozzle section in a state where the cap body is located at the first position. When the mounting tube section of the cap body removed from the syringe body is brought close to the nozzle section of the syringe body, the abutting section of the cap body is pushed in a distal end direction by the distal end section of the nozzle section of the syringe body so as to displace the cap body at the first position to the second position. An inner peripheral surface of the cover member is roughened at least from a vicinity of the distal end of the first tubular section to a vicinity of the proximal end section of the proximal end tubular section.

In accordance with another aspect of the present disclosure, a syringe assembly is disclosed, which includes: the syringe cap described above; and a syringe outer tube constituting the syringe body and being capable of accommodating a drug.

In accordance with a further aspect of the present disclosure, a pre-filled syringe is disclosed, which includes: the syringe assembly described above; a drug filled in the syringe outer tube; and a gasket liquid-tightly slidable in the syringe outer tube in an axial direction.

According to the present disclosure, in an unopened state of the syringe cap, the cap body is at the first position where the viewing section is located in the first space of the substantially opaque first tubular section. In this state, the user cannot visually recognize the viewing section. Whereas, when the mounting tube section of the syringe cap removed from the syringe body is brought close to the nozzle section, the cap body is displaced from the first position to the second position where the viewing section is located in the second space of the second tubular section having the display section. In this state, the user can visually recognize the viewing section via the display section. Therefore, even in a case where the syringe cap once removed from the syringe body is remounted to the syringe body, the user can discriminate between the unopened state and the opened state of the syringe cap.

Further, since the inner peripheral surface of the cover member is roughened at least from a vicinity of the distal end of the first tubular section to a vicinity of the proximal end section of the proximal end tubular section, a frictional resistance when the roughened portion and the outer peripheral surface of the cap body come into contact with each other can be reduced, which allows the cap body to be smoothly displaced from the first position to the second position.

A syringe cap configured to be detachable from and attachable to a syringe body is disclosed, the syringe cap comprising: a cap body; a cover member having a tubular shape and covering the cap body; the cap body includes: a mounting tube section having a tubular shape, having a sealing section configured to seal a drug discharge port of the syringe body at a distal end of the syringe body, and configured to accommodate a nozzle section of the syringe body; an abutting section located at a proximal end section of the mounting tube section and configured to abut with a distal end section of the nozzle section; and a viewing section arranged at a distal end of the mounting tube section; the cover member includes: a first tubular section having an opening at a distal end and a first space configured to internally housing the viewing section; a second tubular section arranged at a distal end of the first tubular section; a proximal end tubular section extending in a proximal end direction from a proximal end of the first tubular section and having a housing space configured to house the mounting tube section; and an engagement protrusion protruding from an inner peripheral surface of a proximal end section of the proximal end tubular section and configured to engage with the proximal end section of the cap body; the second tubular section includes: an annular peripheral wall section extending in a distal end direction from the distal end of the first tubular section; a distal end wall arranged at a distal end of the annular peripheral wall section; and a second space defined by the annular peripheral wall section, the distal end wall, and an inner edge of the distal end of the first tubular section; the annular peripheral wall section includes a display section for visual inspection of an inside of the second space from an outside; and an inner peripheral surface of the cover member includes a plurality of projections and depressions at least from a vicinity of the distal end of the first tubular section to a vicinity of the proximal end section of the proximal end tubular section.

A syringe assembly is disclosed, the syringe assembly comprising: a syringe body, the syringe body including a body section configured to accommodate a drug, and a nozzle section protruding in a distal end direction from a distal end section of the body section and having a drug discharge port at a distal end; and a syringe cap configured to be detachable from and attachable to the syringe body, the syringe cap comprising: a cap body; a cover member having a tubular shape and covering the cap body; the cap body includes: a mounting tube section having a tubular shape, having a sealing section configured to seal a drug discharge port of the syringe body at a distal end of the syringe body, and configured to accommodate a nozzle section of the syringe body; an abutting section located at a proximal end section of the mounting tube section and configured to abut with a distal end section of the nozzle section; and a viewing section arranged at a distal end of the mounting tube section; the cover member includes: a first tubular section having an opening at a distal end and a first space configured to internally housing the viewing section; a second tubular section arranged at a distal end of the first tubular section; a proximal end tubular section extending in a proximal end direction from a proximal end of the first tubular section and having a housing space configured to house the mounting tube section; and an engagement protrusion protruding from an inner peripheral surface of a proximal end section of the proximal end tubular section and configured to engage with the proximal end section of the cap body; the second tubular section includes: an annular peripheral wall section extending in a distal end direction from the distal end of the first tubular section; a distal end wall arranged at a distal end of the annular peripheral wall section; and a second space defined by the annular peripheral wall section, the distal end wall, and an inner edge of the distal end of the first tubular section; the annular peripheral wall section includes a display section for visual inspection of an inside of the second space from an outside; and an inner peripheral surface of the cover member includes a plurality of projections and depressions at least from a vicinity of the distal end of the first tubular section to a vicinity of the proximal end section of the proximal end tubular section.

DETAILED DESCRIPTION

Set forth below with reference to the accompanying drawings is a detailed description of embodiments of a syringe cap, a syringe assembly, and a pre-filled syringe, in which the syringe cap is detachable from a syringe body that includes a body section capable of internally accommodating a drug, and a nozzle section protruding in a distal end direction from a distal end section of the body section and having a drug discharge port at a distal end. Note that since embodiments described below are preferred specific examples of the present disclosure, although various technically preferable limitations are given, the scope of the present disclosure is not limited to the embodiments unless otherwise specified in the following descriptions. In the following description of the pre-filled syringe and components of the pre-filled syringe, the left side in FIG. 1 is referred to as a "distal end", and the right side is referred to as a "proximal end".

Figure 1:
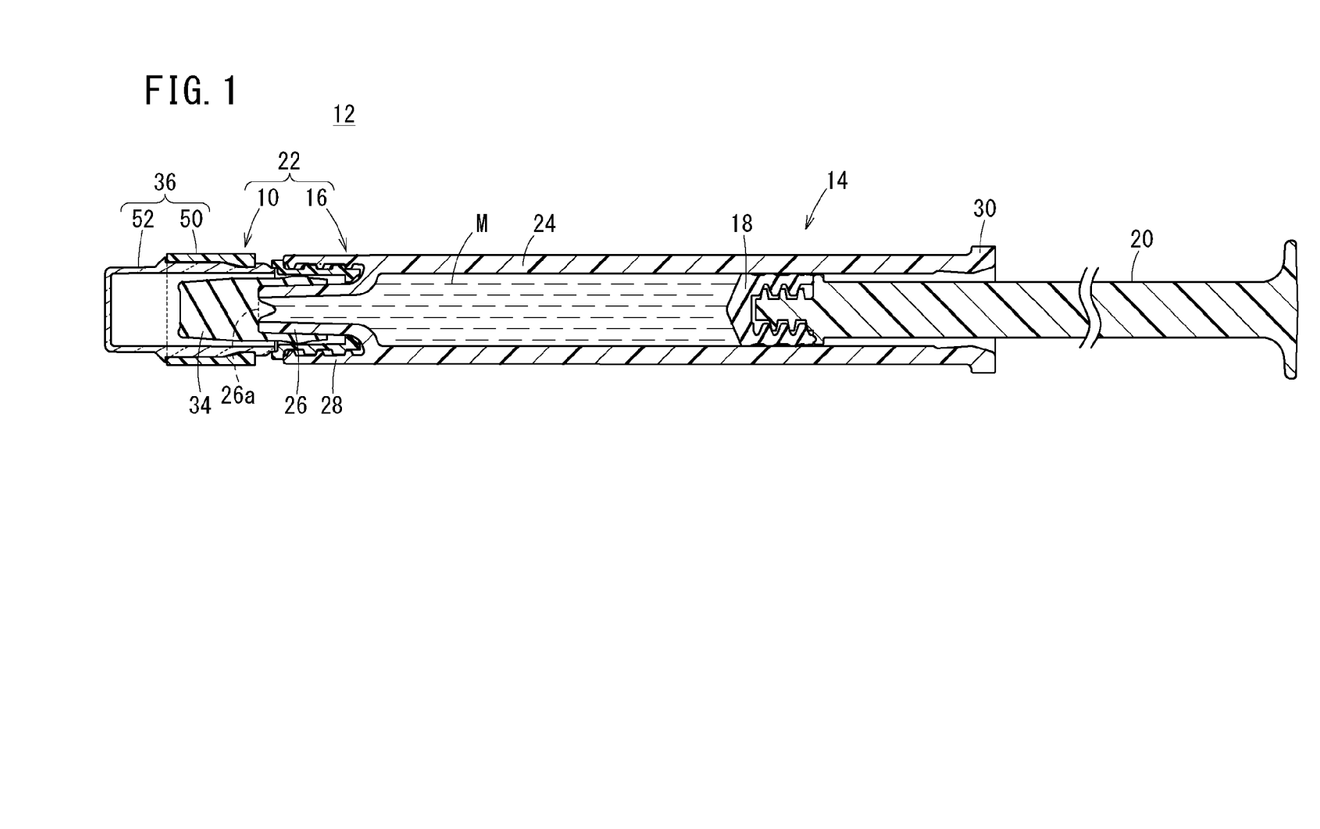
FIG. 1 is a longitudinal cross-sectional view of a pre-filled syringe according to an embodiment of the present disclosure.

As illustrated in FIG. 1, a pre-filled syringe 12 includes a syringe body 14 and a syringe cap 10 (hereinafter, may be simply referred to as a "cap 10") detachably attachable to the syringe body 14. The syringe body 14 includes a syringe outer tube 16, a gasket 18 slidably inserted into the syringe outer tube 16, and a plunger 20 connected to the gasket 18. In the present embodiment, the syringe outer tube 16 and the cap 10 constitute a syringe assembly 22, and the pre-filled syringe 12 is assembled by inserting the gasket 18 connected with the plunger 20 in a state where the syringe outer tube 16 of the syringe assembly 22 is filled with a drug M.

The syringe outer tube 16 can include: a cylindrical body section 24 extending in an axial direction; a hollow nozzle section 26 projecting in the distal end direction from a distal end section of the body section 24; a syringe-side connecting section 28 provided on an outer peripheral side of the nozzle section 26; and a flange section 30 provided at a proximal end section of the body section 24. The body section 24, the nozzle section 26, the syringe-side connecting section 28, and the flange section 30 are integrally formed (i.e., connected together so as to make up a single complete piece or unit).

Figure 2:
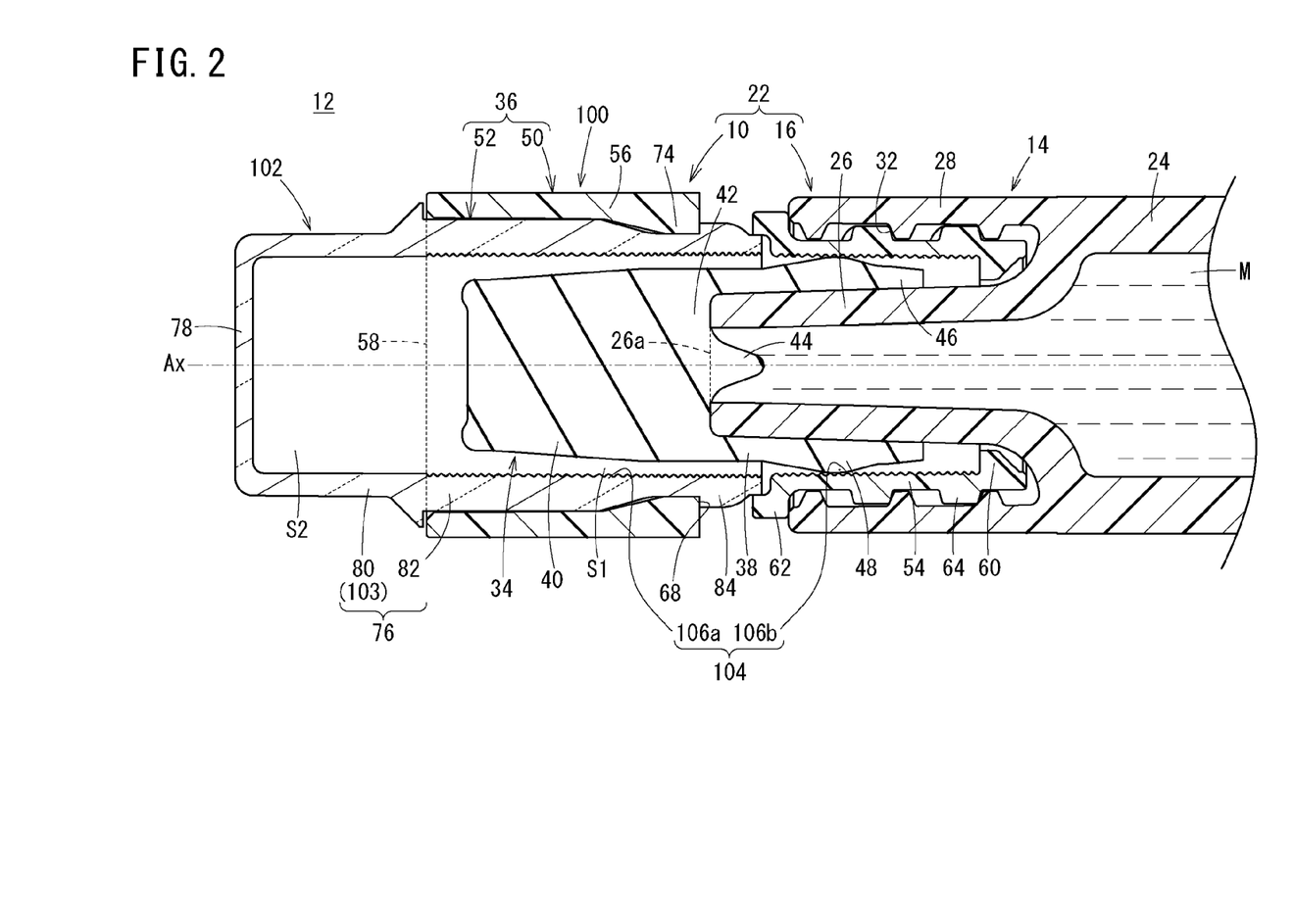
FIG. 2 is a partially omitted enlarged cross-sectional view of a distal end side of the pre-filled syringe of FIG. 1.

As illustrated in FIG. 2, the nozzle section 26 is a cylindrical member provided with a drug discharge port 26a at a distal end, and is configured as a luer connector. The syringe-side connecting section 28 is a lock adapter that projects from a distal end section of the body section 24 to a distal end side concentrically with the nozzle section 26, and has a female screw section 32 formed on an inner peripheral surface. To the syringe-side connecting section 28, the cap 10, an injection needle, and the like are detachably attachable.

A constituent material of the syringe outer tube 16 is not particularly limited, but is preferably form by, for example, polyolefin such as polypropylene, polyurethane, polyethylene, cyclic polyolefin, or polymethylpentene 1, a resin material such as polyester, nylon, polycarbonate, polymethyl methacrylate (PMMA), polyetherimide (PEI), polyethersulfone, polyether ether ketone (PEEK), fluororesin, polyphenylene sulfide (PPS), or a polyacetal resin (POM), a metal material such as stainless steel, glass, or the like.

In FIG. 1, the gasket 18 is liquid-tightly slidable in the syringe outer tube 16 in an axial direction, and feeds the drug M filled in the syringe outer tube 16. A distal end of the plunger 20 is connected to the gasket 18.

Figure 3:
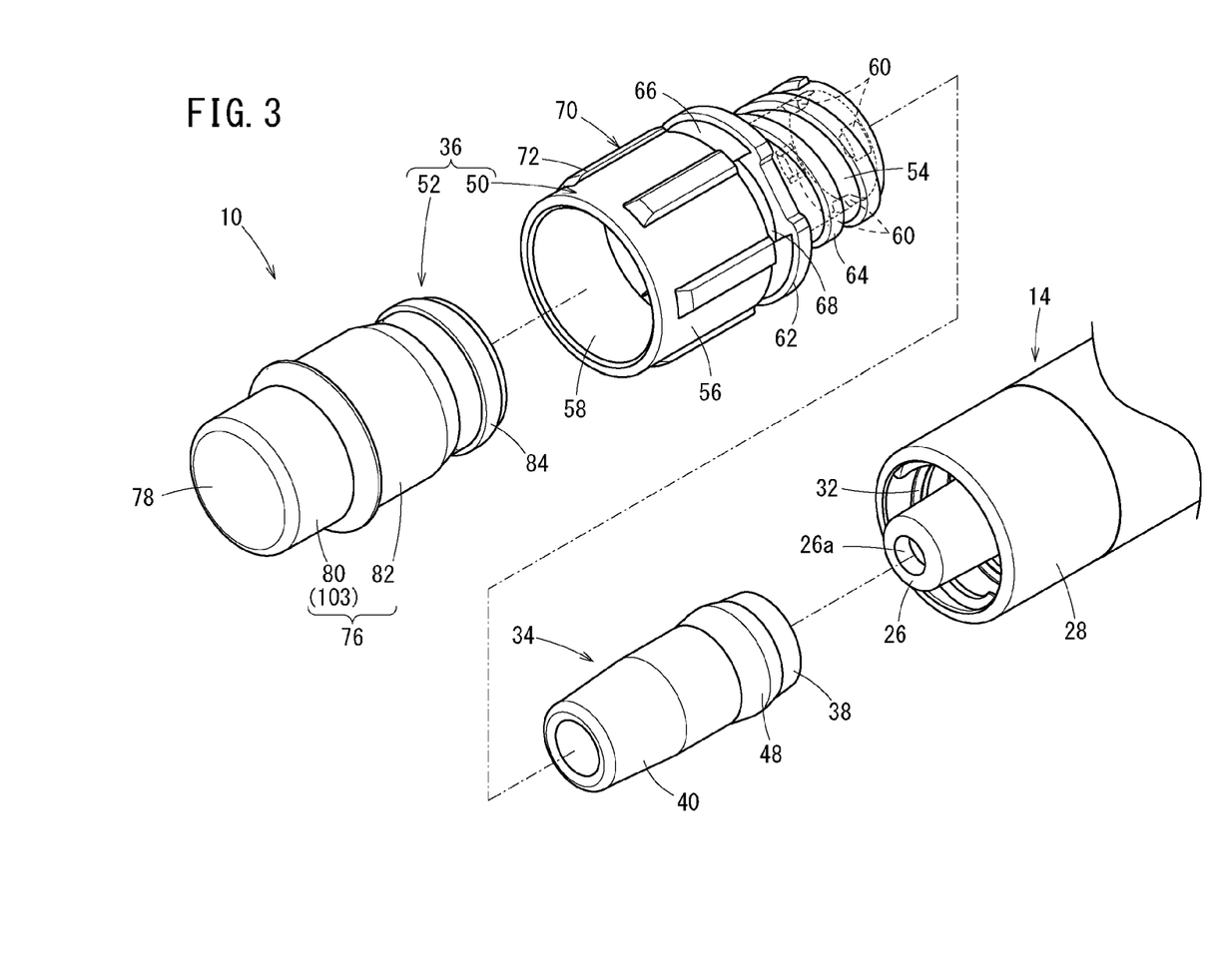
FIG. 3 is an exploded perspective view of FIG. 2.

As illustrated in FIGS. 2 and 3, the cap 10 includes a cap body 34 that closes the drug discharge port 26a of the nozzle section 26 in an unopened state, and a tubular cover member 36 that covers the cap body 34.

Examples of a constituent material of the cap body 34 can include rubber, a synthetic resin elastomer, and the like. Examples of the rubber can include isoprene rubber, butyl rubber, latex rubber, and silicone rubber. As the synthetic resin elastomer, for example, a styrene elastomer, an olefin elastomer, or the like can be used.

The cap body 34 includes a mounting tube section 38 (mounting section) and a viewing section 40 (distal end extending section) extending the distal end direction from a distal end of the mounting tube section 38. The mounting tube section 38 includes a sealing section 42 that is located at a distal end section of the mounting tube section 38 and is capable of liquid-tightly sealing the drug discharge port 26a, and a raised section 44 raised from the sealing section 42. The sealing section 42 seals the drug discharge port 26a by abutting on a distal end section of the nozzle section 26, specifically, a distal end surface of the nozzle section 26 or a side peripheral surface of the distal end section of the nozzle section 26.

The liquid-tightly sealing the drug discharge port 26a means that the drug M does not leak to the outside of the cap body 34. Therefore, even when the sealing section 42 abuts only on the side peripheral surface of the distal end section of the nozzle section 26, the sealing section 42 liquid-tightly seals the drug discharge port 26a.

At the proximal end section of an inner peripheral surface of the mounting tube section 38, an annular abutting protruding section 46 (abutting section) capable of abutting on a distal end section of the nozzle section 26 is provided. In a mounted state (unopened state) in which the cap body 34 is mounted to the nozzle section 26, the abutting protruding section 46 is in contact with an outer peripheral surface of the nozzle section 26 in a compressed and deformed state.

On an outer peripheral surface of the mounting tube section 38, an annular bulging section 48 is provided. The bulging section 48 is a section having a maximum outer diameter of the cap body 34. The bulging section 48 can be compressed and deformed by being sandwiched between the nozzle section 26 and a tubular connecting section 54, in the mounted state of the cap body 34.

In accordance with an exemplary embodiment, the viewing section 40 can be formed, for example, in a cylindrical shape. The viewing section 40 may be colored in a color that is relatively easily recognized by the user, such as red, for example. In accordance with an exemplary embodiment, the coloring of the viewing section 40 may be performed by applying paint to an outer surface of the viewing section 40, or the cap body 34 may be made of rubber or synthetic resin colored in advance.

The cover member 36 includes a tubular member 50 and a distal end cover member 52.

In accordance with an exemplary embodiment, the tubular member 50, for example, can be formed in a cylindrical shape and can be made of a resin material having no transparency (substantially opaque resin material). The tubular member 50 can include: the tubular connecting section 54 (proximal end tubular section) that is located at a proximal end section and is detachable from a syringe side by screwing; a distal end outer tube section 56 extending in the distal end direction from a distal end of the tubular connecting section 54; and an opening 58 provided at a distal end of the distal end outer tube section 56 to expose the cap body 34 from the tubular member 50.

At a proximal end section of an inner peripheral surface of the tubular connecting section 54, a plurality of engagement claw sections 60 (engagement sections, engagement protrusions) extending radially inward are provided. The plurality of engagement claw sections 60 are intermittently provided along a circumferential direction of the tubular connecting section 54. Specifically, the plurality of engagement claw sections 60 can be provided at equal intervals along the circumferential direction of the tubular connecting section 54. In accordance with an exemplary embodiment, an inner diameter of a hole formed by projecting ends (inner end sections) of the plurality of engagement claw sections 60 is smaller than an outer diameter of a proximal end section of the mounting tube section 38 of the cap body 34.

That is, in each of the engagement claw sections 60, a surface directed in the distal end direction is a flat surface extending in a direction orthogonal to a center axis Ax of the cover member 36, and can be in contact with a proximal end surface of the cap body 34. Furthermore, the engagement claw section 60 has an inclined surface inclined inward in the distal end direction on the proximal end side of the engagement claw section 60. As a result, when the cap body 34 is inserted into the tubular member 50 from the proximal end of the tubular member 50 and assembled, the cap body 34 can rather easily get over the engagement claw section 60.

At a proximal end of the distal end outer tube section 56, an insertion regulating section 62 capable of abutting on a distal end of the syringe-side connecting section 28 is provided. The insertion regulating section 62 helps regulate an insertion length of the tubular connecting section 54 between the syringe-side connecting section 28 and the nozzle section 26, by abutting on the distal end of the syringe-side connecting section 28. The tubular connecting section 54 is a cylindrical member provided concentrically with the tubular member 50, and has an outer peripheral surface provided with a male screw section 64 that can be screwed with the female screw section 32.

In FIG. 3, the distal end outer tube section 56 is formed in a size that allows a user to rather easily pick up the distal end outer tube section 56 with fingers of the user. At a proximal end section of the outer peripheral surface of the distal end outer tube section 56, an annular recess 66 is formed. In accordance with an exemplary embodiment, on a bottom surface of the annular recess 66, two through holes 68 are formed. The two through holes 68 are opposed to each other.

On the distal end side from the annular recess 66 on an outer peripheral surface of the distal end outer tube section 56, an anti-slip section 70 functioning as a slip stopper for the user's fingers is formed. The anti-slip section 70 can be formed, for example, by providing a plurality of ribs 72 extending in an axial direction at equal intervals in a circumferential direction. In the present embodiment, for example, six (6) ribs 72 are provided in a circumferential direction of the distal end outer tube section 56. As described above, by setting the number of ribs 72 to six, moldability (injection molding accuracy) of the tubular member 50 can be improved.

In FIG. 2, on the distal end side of the annular recess 66 on an inner peripheral surface of the distal end outer tube section 56, the locking protruding section 74 to lock the distal end cover member 52 protrudes radially inward. Two locking protruding sections 74 can be provided so as to be opposed to each other.

In accordance with an exemplary embodiment, the distal end cover member 52 is formed to have a substantially U-shaped longitudinal cross section, and is to cover the cap body 34 such that the user operating the cap 10 together with the tubular member 50 cannot touch the cap body 34. That is, the distal end cover member 52 has a contact prevention function. The distal end cover member 52 also functions as a detachment prevention section that helps prevent detachment of the cap body 34 from the opening 58 of the tubular member 50.

As illustrated in FIGS. 2 and 3, the distal end cover member 52 can include: the annular section 76 in which a proximal end section is fitted to the distal end outer tube section 56 of the tubular member 50 so as to protrude toward a distal end side from the opening 58 of the tubular member 50; and the distal end wall 78 provided at a distal end section of the annular section 76.

The annular section 76 includes an annular peripheral wall section 80 on the distal end side and a tubular extending inner tube section 82 extending in the proximal end direction from the annular peripheral wall section 80. In accordance with an exemplary embodiment, an inner diameter of the annular section 76 is constant from the distal end to the proximal end, and is larger than an outer diameter of the viewing section 40. In other words, an inner diameter of the distal end cover member 52 is substantially uniform from a distal end of the annular peripheral wall section 80 to a proximal end of the extending inner tube section 82.

In accordance with an exemplary embodiment, the proximal end of the extending inner tube section 82 is in contact with the distal end of the tubular connecting section 54. At a portion corresponding to the annular recess 66 of the tubular member 50 on the outer peripheral surface of the extending inner tube section 82, an annular locking claw 84 to be in contact with the locking protruding section 74 of the tubular member 50 is provided. An outer diameter of the locking claw 84 is larger than a separation interval of the locking protruding section 74. In the present embodiment, the distal end cover member 52 is colorless, but may be colored.

As illustrated in FIG. 2, such a cover member 36 includes a first tubular section 100, the tubular connecting section 54, the engagement claw section 60, and a second tubular section 102. The first tubular section 100 has the opening 58 at a distal end and a first space S1 that can internally accommodate the viewing section 40. In accordance with an exemplary embodiment, the first tubular section 100 is substantially opaque. The first tubular section 100 includes the extending inner tube section 82 forming an inner peripheral section of the first tubular section 100, and the distal end outer tube section 56 forming an outer peripheral section of the first tubular section 100. The tubular connecting section 54 extends in the proximal end direction from a proximal end of the first tubular section 100, and has a space capable of internally housing the mounting tube section 38. The engagement claw section 60 is provided on an inner peripheral surface of the cover member 36, and helps prevent detachment of the cap body 34 in the proximal end direction from the cover member 36, by engaging with the cap body 34.

In accordance with an exemplary embodiment, the second tubular section 102 is substantially transparent as a whole, and extends in the distal end direction from the opening 58 of the first tubular section 100. The second tubular section 102 includes the annular peripheral wall section 80, the distal end wall 78, and a second space S2. The annular peripheral wall section 80 has a display section 103 for visual recognition of the second space S2 from the outside. The display section 103 is formed by substantially the entire annular peripheral wall section 80. The distal end wall 78 is provided at the distal end of the annular peripheral wall section 80. The second space S2 is defined by the annular peripheral wall section 80, the distal end wall 78, and an inner edge of the distal end of the first tubular section 100.

An inner peripheral surface of the cover member 36 has a rough surface section 104 roughened (i.e., having an uneven or an irregular surface) at least from a vicinity of the distal end of the first tubular section 100 to a vicinity of the proximal end section of the tubular connecting section 54. In other words, the rough surface section 104 is provided in a movable range of the bulging section 48 that is a maximum outer diameter section of the cap body 34 on the inner peripheral surface of the cover member 36.

Specifically, the rough surface section 104 extends from a vicinity of the distal end of the extending inner tube section 82 to a vicinity of the proximal end section of the tubular connecting section 54. That is, the rough surface section 104 includes a first rough surface section 106a extending from a vicinity of the distal end to the proximal end of the extending inner tube section 82, and a second rough surface section 106b extending from a vicinity of the distal end of the tubular connecting section 54 to a vicinity of the engagement claw section 60. The first rough surface section 106a extends around an inner peripheral surface of the tubular connecting section 54. The first rough surface section 106a is formed by performing embossing processing on an inner peripheral surface of the extending inner tube section 82. That is, on the first rough surface section 106a, a large number (i.e., a plurality) of projections and depressions are formed. The second rough surface section 106b extends around an inner peripheral surface of the tubular connecting section 54. The second rough surface section 106b is formed by performing embossing processing on the inner peripheral surface of the tubular connecting section 54. On the second rough surface section 106b, a large number of projections and depressions are formed.

In accordance with an exemplary embodiment, the rough surface section 104 is not provided on an inner surface of the second tubular section 102. In other words, the inner surface of the second tubular section 102 (an inner peripheral surface of the annular peripheral wall section 80 and the inner surface of the distal end wall 78) is not roughened, which allows the user to reliably visually recognize the second space S2 via the second tubular section 102. The rough surface section 104 can have a smaller contact resistance than the inner surface of the second tubular section 102 that is not roughened.

In such a pre-filled syringe 12, in an unopened state of the cap 10, the cap body 34 is at a first position where the viewing section 40 is located in the first space S1 of the first tubular section 100. Specifically, the distal end of the cap body 34 is located in the proximal end direction from the opening 58 of the distal end outer tube section 56, and inside the extending inner tube section 82 of the distal end cover member 52. As a result, the outer peripheral section of the viewing section 40 can be hidden by the substantially opaque first tube section (distal end outer tube section 56) and cannot be visually recognized from the outside. Further, the mounting tube section 38 is in a state of being mounted to the nozzle section 26, and the sealing section 42 of the mounting tube section 38 liquid-tightly seals the drug discharge port 26a of the nozzle section 26.

In a case of opening the cap 10 from the syringe body 14, the cover member 36 is pulled out from the syringe outer tube 16 in a state where screwing between the male screw section 64 and the female screw section 32 can be released, which causes the engagement claw section 60 of the tubular connecting section 54 to come into contact with the proximal end surface of the cap body 34. Then, the cap body 34 is pushed in the distal end direction by the tubular connecting section 54, and the mounting tube section 38 is detached from the nozzle section 26, which leads to opening of the cap 10.

Figure 4A:
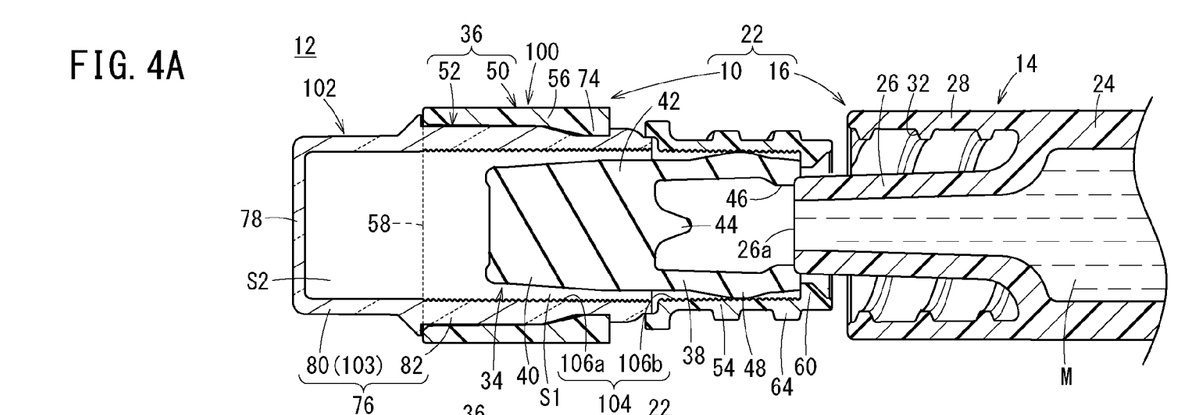
FIG. 4A is a first explanatory view of a recapping operation of a syringe cap.

In a case of recapping the opened cap 10 to the syringe outer tube 16, the distal end section of the nozzle section 26 of the syringe outer tube 16 is inserted into the tubular connecting section 54 from the opening 58 on the proximal end side of the tubular connecting section 54, which causes the distal end section of the nozzle section 26 to come into contact with the abutting protruding section 46 of the cap body 34 (see FIG. 4A).

Subsequently, when the tubular member 50 and the syringe outer tube 16 are brought close to each other, by the abutting protruding section 46 of the cap body 34 abutting with the distal end section of the nozzle section 26, the cap body 34 at the first position is displaced in the distal end direction with respect to the tubular member 50 by being pushed by the nozzle section 26, and the viewing section 40 protrudes toward the distal end side from the opening 58 on the distal end side of the tubular member 50.

Figure 4B:
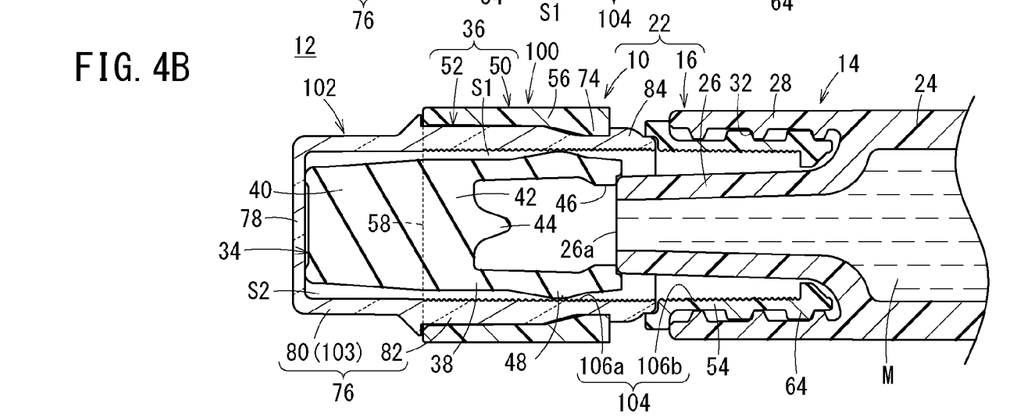
FIG. 4B is a second explanatory view of the recapping operation of the syringe cap.

Then, by screwing the male screw section 64 of the tubular connecting section 54 with the female screw section 32 of the syringe-side connecting section 28, the opened cap 10 is recapped (remounted) to the syringe outer tube 16. At this time, the cap body 34 is at the second position where the viewing section 40 is located in the second space S2 of the second tubular section 102 (on the distal end side from the opening 58 of the distal end outer tube section 56) (see FIG. 4B). Therefore, the outer peripheral section of the viewing section 40 can be visually recognized from the outside via the transparent second tubular section 102 (distal end cover member 52).

In this case, the cap 10, the syringe assembly 22, and the pre-filled syringe 12 according to the present embodiment have the following effects.

In the cap 10, in an unopened state of the syringe cap 10, the cap body 34 is at the first position where the viewing section 40 is located in the first space S1 of the substantially opaque first tubular section 100. In this state, the user cannot visually recognize the viewing section 40. Whereas, when the mounting tube section 38 of the syringe cap 10 removed from the syringe body 14 is brought close to the nozzle section 26, the cap body 34 is displaced from the first position to the second position where the viewing section 40 is located in the second space S2 of the second tubular section 102 having the display section 103. In this state, the user can visually recognize the viewing section 40 via the display section 103. Therefore, even in a case where the syringe cap 10 once removed from the syringe body 14 is remounted to the syringe body 14, the user can discriminate between the unopened state and the opened state of the syringe cap 10.

Further, since the inner peripheral surface of the cover member 36 is roughened at least from a vicinity of the distal end of the first tubular section 100 to a vicinity of the proximal end section of the tubular connecting section 54, a frictional resistance when the roughened portion (rough surface section 104) and the outer peripheral surface of the cap body 34 come into contact with each other can be reduced. As a result, the cap body 34 can be rather smoothly moved from the first position to the second position.

In accordance with an exemplary embodiment, the inner peripheral surface of the cover member 36 can be roughened to a vicinity of the engagement claw section 60.

According to such a configuration, the engagement claw section 60 does not become an obstacle when the cap body 34 is displaced from the first position to the second position. In addition, the cap body 34 in a state of being engaged with the engagement claw section 60 is to be rather easily moved to the second position.

In accordance with an exemplary embodiment, the annular peripheral wall section 80 of the second tubular section 102 is substantially transparent such that substantially the entire annular peripheral wall section 80 serves as the display section 103, and an inner peripheral surface of the annular peripheral wall section 80 is not roughened.

According to such a configuration, the user can rather easily visually recognize a state where the viewing section 40 is located at the second position while rather smoothly moving the cap body 34 from the first position to the second position.

In accordance with an exemplary embodiment, an inner diameter of the cover member 36 can be substantially uniform from a vicinity of the distal end of the annular peripheral wall section 80 to a vicinity of the engagement claw section 60.

According to such a configuration, since a step is not substantially formed on the inner peripheral surface of the cover member 36 from the first space S1 to the second space S2, the cap body 34 can be rather smoothly moved.

The cover member 36 includes the substantially opaque tubular member 50 and the substantially transparent distal end cover member 52. The tubular member 50 has: the distal end outer tube section 56 constituting the outer peripheral section of the first tubular section 100; and the tubular connecting section 54. The distal end cover member 52 has the second tubular section 102, and the extending inner tube section 82 extending from the proximal end of the annular peripheral wall section 80 of the second tubular section 102 into the tubular member 50 and forming an inner peripheral section of the first tubular section 100. In accordance with an exemplary embodiment, the display section 103 can be formed by substantially the entire annular peripheral wall section 80, and the inner peripheral surface of the cover member 36 is roughened at least from a vicinity of the distal end of the extending inner tube section 82 to a vicinity of the proximal end section of the tubular connecting section 54.

According to such a configuration, it is possible to reliably roughen a part of the inner peripheral surface of the cover member 36 while simplifying the configuration of the display section 103.

The cap 10, the syringe assembly 22, and the pre-filled syringe 12 according to the present disclosure are not limited to the above-described embodiment, and it is a matter of course that various configurations can be adopted without departing from the gist of the present disclosure.

In accordance with an exemplary embodiment, the tubular member 50 and the distal end cover member 52 may be integrally molded by one substantially opaque member. As a result, the inner peripheral surface of the extending inner tube section 82 and the inner peripheral surface of the tubular connecting section 54 form one continuous inner peripheral surface without a step. In this case, for example, by forming a hole having such a size that a user's finger cannot be inserted into the second tubular section 102, the hole may be made to function as the display section. The tubular member 50 and the distal end cover member 52 may be integrally molded by one substantially transparent member. In this case, for example, the outer peripheral surface of the first tubular section 100 may be covered with a substantially opaque cover member (mask member), to help prevent the viewing section 40 from being visually recognized in a state where the cap body 34 is at the first position.

The present disclosure may be, for example, the pre-filled syringe 12 having no plunger 20. In this case, to the pre-filled syringe 12, a pressing member that presses the gasket 18 in the distal end direction is separately mounted. In addition, the cap 10, the syringe assembly 22, or the pre-filled syringe 12 in which the abutting protruding section 46 is omitted from the cap body 34 may be adopted. In this case, by making an inner diameter of the opening on the proximal end side of the mounting tube section 38 smaller than a distal end outer diameter of the nozzle section 26 of the syringe outer tube 16, the proximal end of the mounting tube section 38 functions as an abutting section that can abut on the distal end section of the nozzle section 26.

Further, the cap body 34 may be configured such that the viewing section 40 does not include the distal end of the cap body 34, and the distal end of the cap body 34 protrudes to the distal end side from the opening 58 of the tubular member 50, at the first position. In this case, the viewing section 40 of the cap body 34 is provided so as to be located in the distal end outer tube section 56 of the tubular member 50 when the cap body 34 is at the first position, and to protrude from the opening 58 of the tubular member 50 when the cap body 34 is at the second position.

Examples of such a viewing section 40 can include: a viewing section formed by coloring an outer peripheral surface that is slightly on the proximal end side from the distal end of the cap body 34 in red or the like, a viewing section formed by a colored member fitted so as to cover an outer peripheral section that is slightly on the proximal end side from the distal end of the distal end protruding section of the cap body 34; and the like. Even with such a configuration, the user can rather easily and reliably discriminate between the unopened state and the recapped state of the cap 10.

In the distal end wall 78 of the distal end cover member 52, a hole having such a size that a user's finger cannot be inserted may be formed. In a case where such a hole is formed on the distal end wall 78, by inserting a jig into the hole of the distal end wall 78 and pushing the cap body 34 into the nozzle section 26, the previously assembled cap 10 can be mounted to the syringe outer tube 16.

In a state where the cap 10 is removed from the syringe body 14, the cap body 34 is movable from the first position to the second position without the mounting section (mounting tube section 38) being pushed by the nozzle section 26. Therefore, in a case where the cap 10 removed from the syringe body 14 is remounted to the syringe body 14 in a state where the cap body 34 is arranged at the second position, displacement of the cap body 34 from the first position to the second position does not occur. Even in this case, when the mounting section (mounting tube section 38) of the cap body 34 arranged at the second position abuts on the nozzle section 26, displacement of the cap body 34 from the second position to the first position can be regulated, and the viewing section 40 is located at the second position. Therefore, the user can rather easily and reliably discriminate between the unopened state and the opened state of the cap 10.

The above embodiment is summarized as follows.

In the above embodiment, there is disclosed a syringe cap 10 detachably attachable to a syringe body 14 including: a body section 24 capable of internally accommodating a drug M; and a nozzle section 26 protruding in a distal end direction from a distal end section of the body section 24 and having a drug discharge port 26a at a distal end, in which the syringe cap 10 includes: a cap body 34 made by an elastic material; and a cover member 36 having a tubular shape and covering the cap body 34, the cap body 34 includes: a mounting tube section 38 having a tubular shape, having a sealing section 42 that liquid-tightly seals the drug discharge port 26a at a distal end, and being capable of accommodating the nozzle section 26; an abutting section 46 located at a proximal end section of the mounting tube section 38 and being capable of abutting with a distal end section of the nozzle section 26; and a viewing section 40 arranged at a distal end of the mounting tube section 38, the cover member 36 includes: a first tubular section 100 being substantially opaque, and having an opening 58 at a distal end and a first space S1 capable of internally housing the viewing section 40; a second tubular section 102 arranged at a distal end of the first tubular section 100; a proximal end tubular section 54 extending in a proximal end direction from a proximal end of the first tubular section 100 and having a housing space capable of internally housing the mounting tube section 38; and an engagement protrusion 60 protruding from an inner peripheral surface of a proximal end section of the proximal end tubular section 54 and configured to engage with the proximal end section of the cap body 34 to prevent detachment of the cap body 34 in a proximal end direction from the cover member 36, the second tubular section 102 has: an annular peripheral wall section 80 extending in a distal end direction from the distal end of the first tubular section 100; a distal end wall 78 arranged at a distal end of the annular peripheral wall section 80; and a second space S2 defined by the annular peripheral wall section 80, the distal end wall 78, and an inner edge of the distal end of the first tubular section 100, the annular peripheral wall section 80 has a display section 103 for visual inspection of an inside of the second space S2 from an outside, the cap body 34 can displace, along a center axis Ax of the cover member 36 in the cover member 36, from a first position where the viewing section 40 is located in the first space S1 of the first tubular section 100 to a second position where the viewing section 40 is arranged in the second space S2, the sealing section 42 is capable of liquid-tightly sealing the nozzle section 26 in a state where the cap body 34 is located at the first position, when the mounting tube section 38 of the cap body 34 removed from the syringe body 14 is brought close to the nozzle section 26 of the syringe body 14, the abutting section 46 of the cap body 34 is pushed in a distal end direction by the distal end section of the nozzle section 26 of the syringe body 14 so as to displace the cap body 34 at the first position to the second position, and an inner peripheral surface of the cover member 36 is roughened at least from a vicinity of the distal end of the first tubular section 100 to a vicinity of the proximal end section of the proximal end tubular section 54.

In the syringe cap 10 described above, the inner peripheral surface of the cover member 36 may be roughened to a vicinity of the engagement protrusion 60.

In the syringe cap 10 described above, the annular peripheral wall section 80 of the second tubular section 102 may be substantially transparent such that substantially the entire annular peripheral wall section 80 serves as the display section 103, and an inner peripheral surface of the annular peripheral wall section 80 may not be roughened.

In the syringe cap 10 described above, the inner diameter of the cover member 36 may be substantially uniform from a vicinity of a distal end of the annular peripheral wall section 80 to a vicinity of the engagement protrusion 60.

In the syringe cap 10 described above, the cover member 36 may include: a tubular member 50 that is substantially opaque; and a distal end cover member 52 that is substantially transparent, the tubular member 50 may have: a distal end outer tube section 56 constituting an outer peripheral section of the first tubular section 100; and a proximal end tubular section 54, the distal end cover member 52 may have: a second tubular section 102; and an extending inner tube section 82 extending from a proximal end of the annular peripheral wall section 80 of the second tubular section 102 into the tubular member 50 and forming an inner peripheral section of the first tubular section 100, the display section 103 may be formed by substantially the entire annular peripheral wall section 80, and an inner peripheral surface of the cover member 36 may be roughened at least from a vicinity of the distal end of the extending inner tube section 82 to a vicinity of the proximal end section of the proximal end tubular section 54.

In the syringe cap 10 described above, the syringe body 14 may include a lock adapter 28 having a tubular shape, having a female screw section 32 on an inner peripheral surface, and covering an outer peripheral section of the nozzle section 26, the proximal end tubular section 54 of the cover member 36 may be a tubular connecting section 54 that can be inserted between the lock adapter 28 and the nozzle section 26, the tubular connecting section 54 may have, on an outer peripheral section of the tubular connecting section 54, a male screw section 64 capable of being screwed with the female screw section 32 of the lock adapter 28, in a state where the syringe cap 10 is mounted to the syringe body 14 by screwing between the male screw section 64 of the tubular connecting section 54 and the female screw section 32 of the lock adapter 28, and the cap body 34 is located at the first position, the mounting tube section 38 may be inserted between the tubular connecting section 54 and the nozzle section 26, and the sealing section 42 may liquid-tightly seal the drug discharge port 26a, and when the male screw section 64 of the tubular connecting section 54 is screwed with the female screw section 32 of the lock adapter 28 in a state where the syringe cap 10 is removed from the syringe body 14, the cap body 34 may be displaced from the first position to the second position by the abutting section 46 of the cap body 34 being pushed by the distal end section of the nozzle section 26.

The above embodiment discloses a syringe assembly 22 including the syringe cap 10 described above and a syringe outer tube 16 constituting the syringe body 14 and being capable of accommodating a drug M.

The above embodiment discloses a pre-filled syringe 12 including the syringe assembly 22 described above, a drug M filled in the syringe outer tube 16, and a gasket 18 liquid-tightly slidable in the syringe outer tube 16 in an axial direction.

The detailed description above describes embodiments of a syringe cap, a syringe assembly, and a pre-filled syringe, in which the syringe cap is detachable from a syringe body that includes: a body section capable of internally accommodating a drug; and a nozzle section protruding in a distal end direction from a distal end section of the body section and having a drug discharge port at a distal end. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe cap configured to be detachable from and attachable to a syringe body, the syringe body including a body section configured to internally accommodate a drug, and a nozzle section protruding in a distal end direction from a distal end section of the body section and having a drug discharge port at a distal end, the syringe cap comprising:
   a cap body made from an elastic material;
   a cover member having a tubular shape and covering the cap body;
   the cap body includes:
      a mounting tube section having a tubular shape, having a sealing section that liquid-tightly seals the drug discharge port at a distal end, and being capable of accommodating the nozzle section;
      an abutting section located at a proximal end section of the mounting tube section and being capable of abutting with a distal end section of the nozzle section; and
      a viewing section arranged at a distal end of the mounting tube section;
   the cover member includes:
      a first tubular section being substantially opaque, and having an opening at a distal end and a first space capable of internally housing the viewing section;
      a second tubular section arranged at a distal end of the first tubular section;
      a proximal end tubular section extending in a proximal end direction from a proximal end of the first tubular section and having a housing space capable of internally housing the mounting tube section; and an engagement protrusion protruding from an inner peripheral surface of a proximal end section of the proximal end tubular section and configured to engage with the proximal end section of the cap body to prevent detachment of the cap body in a proximal end direction from the cover member;

the second tubular section includes:
an annular peripheral wall section extending in a distal end direction from the distal end of the first tubular section;
a distal end wall arranged at a distal end of the annular peripheral wall section; and
a second space defined by the annular peripheral wall section, the distal end wall, and an inner edge of the distal end of the first tubular section;

the annular peripheral wall section includes a display section for visual inspection of an inside of the second space from an outside;

the cap body configured to displace, along a center axis of the cover member in the cover member, from a first position where the viewing section is located in the first space of the first tubular section to a second position where the viewing section is arranged in the second space;

the sealing section is capable of liquid-tightly sealing the nozzle section in a state where the cap body is located at the first position;

when the mounting tube section of the cap body removed from the syringe body is brought close to the nozzle section of the syringe body, the abutting section of the cap body is pushed in a distal end direction by the distal end section of the nozzle section of the syringe body so as to displace the cap body at the first position to the second position; and an inner peripheral surface of the cover member is roughened at least from a vicinity of the distal end of the first tubular section to a vicinity of the proximal end section of the proximal end tubular section.

2. The syringe cap according to claim 1, wherein the inner peripheral surface of the cover member is roughened to a vicinity of the engagement protrusion.

3. The syringe cap according to claim 1, wherein the annular peripheral wall section of the second tubular section is substantially transparent such that substantially a whole of the annular peripheral wall section serves as the display section, and an inner peripheral surface of the annular peripheral wall section is not roughened.

4. The syringe cap according to claim 1, wherein an inner diameter of the cover member is substantially uniform from a vicinity of a distal end of the annular peripheral wall section to a vicinity of the engagement protrusion.

5. The syringe cap according to claim 1, wherein
the cover member includes:
a tubular member that is substantially opaque; and
a distal end cover member that is substantially transparent;
the tubular member includes:
a distal end outer tube section constituting an outer peripheral section of the first tubular section and the proximal end tubular section;
the distal end cover member includes:
the second tubular section; and
an extending inner tube section extending from a proximal end of the annular peripheral wall section of the second tubular section into the tubular member and forming an inner peripheral section of the first tubular section;

the display section is formed by substantially a whole of the annular peripheral wall section; and an inner peripheral surface of the cover member is roughened at least from a vicinity of a distal end of the extending inner tube section to a vicinity of the proximal end section of the proximal end tubular section.

6. The syringe cap according to claim 1, wherein
the syringe body includes a lock adapter having a tubular shape, having a female screw section on an inner peripheral surface, and covering an outer peripheral section of the nozzle section;
the proximal end tubular section of the cover member is a tubular connecting section that is able to be inserted between the lock adapter and the nozzle section;
the tubular connecting section has a male screw section capable of being screwed with the female screw section of the lock adapter, on an outer peripheral section of the tubular connecting section;
in a state where the syringe cap is mounted to the syringe body by screwing between the male screw section of the tubular connecting section and the female screw section of the lock adapter, and the cap body is located at the first position, the mounting tube section is inserted between the tubular connecting section and the nozzle section, and the sealing section liquid-tightly seals the drug discharge port; and
when the male screw section of the tubular connecting section is screwed with the female screw section of the lock adapter in a state where the syringe cap is removed from the syringe body, the cap body is displaced from the first position to the second position by the abutting section of the cap body being pushed by the distal end section of the nozzle section.

7. The syringe cap according to claim 1, wherein the roughened inner peripheral surface of the cover member includes a plurality of projections and depressions.

8. A syringe assembly comprising:
the syringe cap according to claim 1; and
a syringe outer tube constituting the syringe body and being configured to accommodate the drug.

9. A pre-filled syringe comprising:
the syringe assembly according to claim 8;
the drug filled in the syringe outer tube; and
a gasket liquid-tightly slidable in the syringe outer tube in an axial direction.

10. A syringe cap configured to be detachable from and attachable to a syringe body, the syringe cap comprising:
a cap body;
a cover member having a tubular shape and covering the cap body;
the cap body includes:
a mounting tube section having a tubular shape, having a sealing section configured to seal a drug discharge port of the syringe body at a distal end of the syringe body, and configured to accommodate a nozzle section of the syringe body;
an abutting section located at a proximal end section of the mounting tube section and configured to abut with a distal end section of the nozzle section; and
a viewing section arranged at a distal end of the mounting tube section;
the cover member includes:
a first tubular section having an opening at a distal end and a first space configured to internally housing the viewing section;
a second tubular section arranged at a distal end of the first tubular section;

a proximal end tubular section extending in a proximal end direction from a proximal end of the first tubular section and having a housing space configured to house the mounting tube section; and an engagement protrusion protruding from an inner peripheral surface of a proximal end section of the proximal end tubular section and configured to engage with the proximal end section of the cap body;

the second tubular section includes:

an annular peripheral wall section extending in a distal end direction from the distal end of the first tubular section;

a distal end wall arranged at a distal end of the annular peripheral wall section; and a second space defined by the annular peripheral wall section, the distal end wall, and an inner edge of the distal end of the first tubular section;

the annular peripheral wall section includes a display section for visual inspection of an inside of the second space from an outside; and an inner peripheral surface of the cover member includes a plurality of projections and depressions at least from a vicinity of the distal end of the first tubular section to a vicinity of the proximal end section of the proximal end tubular section;

the cap body configured to displace, along a center axis of the cover member in the cover member, from a first position where the viewing section is located in the first space of the first tubular section to a second position where the viewing section is arranged in the second space;

the sealing section is capable of liquid-tightly sealing the nozzle section in a state where the cap body is located at the first position; and when the mounting tube section of the cap body removed from the syringe body is brought close to the nozzle section of the syringe body, the abutting section of the cap body is pushed in a distal end direction by the distal end section of the nozzle section of the syringe body so as to displace the cap body at the first position to the second position.

11. The syringe cap according to claim 10, wherein the inner peripheral surface of the cover member includes a plurality of projections and depressions to a vicinity of the engagement protrusion.

12. The syringe cap according to claim 10, wherein an inner peripheral surface of the annular peripheral wall section does not include a plurality of projections and depressions.

13. The syringe cap according to claim 10, wherein an inner diameter of the cover member is substantially uniform from a vicinity of a distal end of the annular peripheral wall section to a vicinity of the engagement protrusion.

14. The syringe cap according to claim 10, wherein the cover member includes:

a distal end outer tube section constituting an outer peripheral section of the first tubular section; and the proximal end tubular section;

the distal end cover member includes:

the second tubular section; and an extending inner tube section extending from a proximal end of the annular peripheral wall section of the second tubular section into the tubular member and forming an inner peripheral section of the first tubular section;

the display section is formed by substantially a whole of the annular peripheral wall section; and an inner peripheral surface of the cover member that includes a plurality of projections and depression at least from a vicinity of a distal end of the extending inner tube section to a vicinity of the proximal end section of the proximal end tubular section.

15. The syringe cap according to claim 10 wherein the syringe body includes a lock adapter having a tubular shape, having a female screw section on an inner peripheral surface, and covering an outer peripheral section of the nozzle section;

the proximal end tubular section of the cover member is a tubular connecting section that is able to be inserted between the lock adapter and the nozzle section;

the tubular connecting section has a male screw section capable of being screwed with the female screw section of the lock adapter, on an outer peripheral section of the tubular connecting section;

in a state where the syringe cap is mounted to the syringe body by screwing between the male screw section of the tubular connecting section and the female screw section of the lock adapter, and the cap body is located at the first position, the mounting tube section is inserted between the tubular connecting section and the nozzle section, and the sealing section liquid-tightly seals the drug discharge port; and when the male screw section of the tubular connecting section is screwed with the female screw section of the lock adapter in a state where the syringe cap is removed from the syringe body, the cap body is displaced from the first position to the second position by the abutting section of the cap body being pushed by the distal end section of the nozzle section.

16. A syringe assembly, the syringe assembly comprising:

a syringe body, the syringe body including a body section configured to accommodate a drug, and a nozzle section protruding in a distal end direction from a distal end section of the body section and having a drug discharge port at a distal end; and a syringe cap configured to be detachable from and attachable to the syringe body, the syringe cap comprising:

a cap body;

a cover member having a tubular shape and covering the cap body;

the cap body includes:

a mounting tube section having a tubular shape, having a sealing section configured to seal the drug discharge port of the syringe body at a distal end of the syringe body, and configured to accommodate the nozzle section of the syringe body;

an abutting section located at a proximal end section of the mounting tube section and configured to abut with a distal end section of the nozzle section; and a viewing section arranged at a distal end of the mounting tube section;

the cover member includes:

a first tubular section having an opening at a distal end and a first space configured to internally housing the viewing section;

a second tubular section arranged at a distal end of the first tubular section;

a proximal end tubular section extending in a proximal end direction from a proximal end of the first tubular section and having a housing space configured to house the mounting tube section; and an engagement protrusion protruding from an inner peripheral surface of a proximal end section of the proximal end tubular section and configured to engage with the proximal end section of the cap body;

the second tubular section includes:
- an annular peripheral wall section extending in a distal end direction from the distal end of the first tubular section;
- a distal end wall arranged at a distal end of the annular peripheral wall section; and
- a second space defined by the annular peripheral wall section, the distal end wall, and an inner edge of the distal end of the first tubular section;

the annular peripheral wall section includes a display section for visual inspection of an inside of the second space from an outside;

an inner peripheral surface of the cover member includes a plurality of projections and depressions at least from a vicinity of the distal end of the first tubular section to a vicinity of the proximal end section of the proximal end tubular section;

the cap body configured to displace, along a center axis of the cover member in the cover member, from a first position where the viewing section is located in the first space of the first tubular section to a second position where the viewing section is arranged in the second space;

the sealing section is capable of liquid-tightly sealing the nozzle section in a state where the cap body is located at the first position; and when the mounting tube section of the cap body removed from the syringe body is brought close to the nozzle section of the syringe body, the abutting section of the cap body is pushed in a distal end direction by the distal end section of the nozzle section of the syringe body so as to displace the cap body at the first position to the second position.

17. The syringe assembly according to claim 16, wherein the inner peripheral surface of the cover member includes a plurality of projections and depressions to a vicinity of the engagement protrusion.

18. A pre-filled syringe comprising:
- the syringe assembly according to claim 16;
- the drug filled in the syringe outer tube; and
- a gasket liquid-tightly slidable in the syringe outer tube in an axial direction.

* * * * *